US00PP24017P2

(12) United States Plant Patent
Stemkens

(10) Patent No.: US PP24,017 P2
(45) Date of Patent: Nov. 5, 2013

(54) ***SAXIFRAGA* PLANT NAMED 'SAXZ0006'**

(50) Latin Name: *Saxifraga×arendsii*
Varietal Denomination: SAXZ0006

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 69 days.

(21) Appl. No.: 13/385,031

(22) Filed: Jan. 30, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Kent L Bell
(74) *Attorney, Agent, or Firm* — Joshua L. Prince

(57) ABSTRACT

A new *Saxifraga* plant, particularly distinguished by the greyed-purple flower color, light green pubescent foliage, with compact and mounded plant habit.

1 Drawing Sheet

Latin name of the genus and species of the plant claimed: *Saxifraga×arendsii*.

Varietal denomination: 'SAXZ0006'.

BACKGROUND OF THE NEW PLANT

The present invention comprises a new *Saxifraga*, botanically known as *Saxifraga×arendsii*, and hereinafter referred to by the variety name 'SAXZ0006'.

'SAXZ0006' is a product of a planned breeding program. The new cultivar has greyed-purple flower color, light green pubescent foliage, with compact and mounded plant habit.

'SAXZ0006' originates from an open pollination cross made in a controlled breeding program in a greenhouse in Enkhuizen, Netherlands. The female parent was the proprietary plant designated 'F0571-33', unpatented, with red flowers with pointed petals, and glabrous foliage.

The male parent of 'SAXZ0006' was an unknown plant. The resultant seed were sown in August 2005 Enkhuizen, Netherlands.

'SAXZ0006' was selected as one flowering plant within the progeny of the stated cross in March 2006 in a controlled environment in Enkhuizen, Netherlands.

The first act of asexual reproduction of 'SAXZ0006' was accomplished when vegetative cuttings were propagated from the initial selected plant in April 2005 in a controlled environment in Enkhuizen, Netherlands.

BRIEF SUMMARY OF INVENTION

Horticultural examination of plants grown from cuttings of the plant initiated in April 2005 in Enkhuizen, Netherlands, and continuing thereafter, has demonstrated that the combination of characteristics as herein disclosed for 'SAXZ0006' are firmly fixed and are retained through successive generations of asexual reproduction.

'SAXZ0006' has not been observed under all possible environmental conditions. The phenotype may vary significantly with variations in environment such as temperature, light intensity, and day length.

A Plant Breeder's Right for this cultivar was applied for in the European Union on May 19, 2011, No. 2011/1305.

'SAXZ0006' has not been made publicly available more than one year prior to the filing of this application.

The following traits have been repeatedly observed and are determined to be basic characteristics of the new variety. The combination of these characteristics distinguishes this *Saxifraga* as a new and distinct variety.

BRIEF DESCRIPTION OF THE PHOTOGRAPHS

The accompanying photographic drawing shows typical flower and foliage characteristics of 'SAXZ0006' with colors being as true as possible with an illustration of this type.

Figure 1:
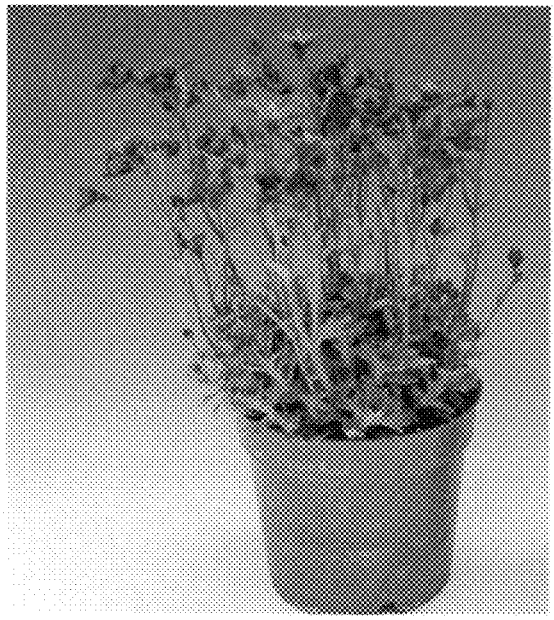
Figure 2:
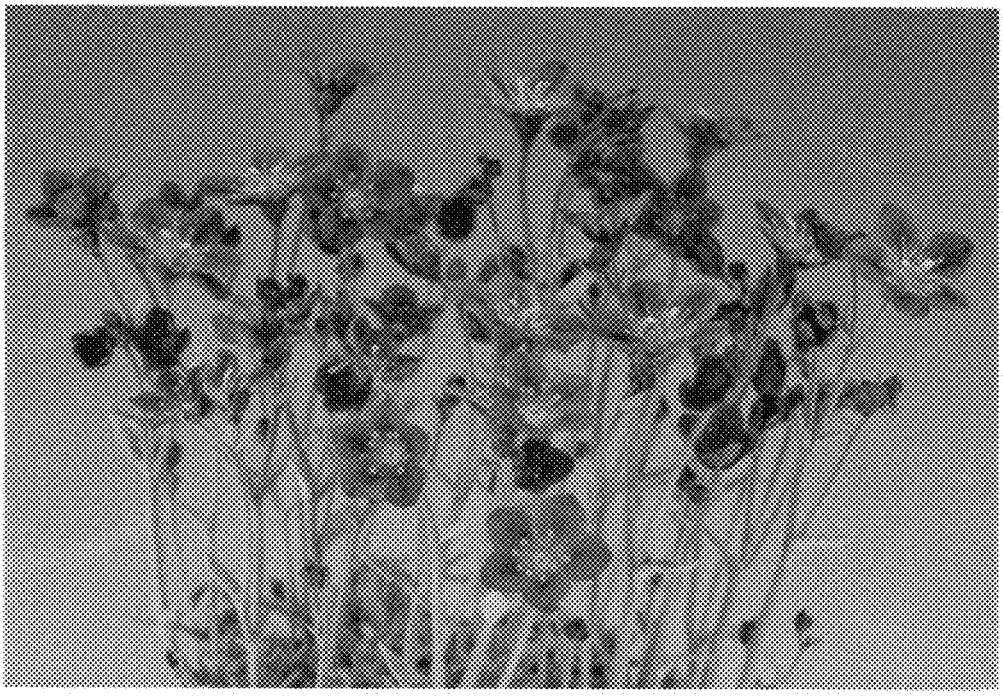

The photographic drawing shows in FIG. 1 a flowering plant of the new variety and in FIG. 2 a close-up of inflorescences.

DETAILED BOTANICAL DESCRIPTION

The plant description, measurements, and aforementioned photographs were taken in Enkhuizen, Netherlands in March 2011. Plants were growing in 11 cm containers and were 28 weeks of age.

Color Chart used: Royal Horticultural Society Colour Chart (R.H.S.) 2001

TABLE 1

DIFFERENCES BETWEEN THE NEW VARIETY 'SAXZ0006' AND A SIMILAR VARIETY

| | 'SAXZ0006' | 'Rockred' (U.S. Plant Pat. No. 19,643) |
|---|---|---|
| Flower color: | Greyed purple | Red-purple |
| Leaf texture: | Pubescent | Glabrous |
| Leaf shape: | Ovate with 3 narrow lobes | 3 broad lobes |

Plant:

*Form, growth and habit.*—Compact and mats of rosettes; each rosette develops several short branches and flower stems, with one or more inflorescences.

*Plant height.*—15.0 cm.

*Plant height (inflorescence included).*—20.0 cm.

*Plant width.*—22.0 cm.

Roots:
*Number of days to initiate roots*.—About 12-14 days at about 18 degrees C.
*Number of days to produce a rooted cutting*.—About 4 weeks at 18 degrees C.
*Type*.—Fine, fibrous, free branching.
*Color*.—Closest to RHS 155C.

Foliage:
*Type*.—Alternate.
*Immature, leaf color, upper surface*.—RHS 137B.
*Lower surface*.—RHS 137A.
*Mature, leaf color, upper surface*.—RHS 143B.
*Lower surface*.—RHS 143C.
*Length*.—1.5-2.0 cm.
*Width*.—1.0-1.3 cm.
*Shape*.—Overall ovate, with 3 narrow lobes.
*Base shape*.—Attenuate.
*Apex shape*.—Mucronulate.
*Margin*.—Palmately lobed; entire.
*Texture, upper surface*.—Pubescent.
*Lower surface*.—Slightly pubescent.
*Color of veins, upper surface*.—RHS 143B.
*Color of veins, lower surface*.—RHS 143C.
*Petioles color*.—RHS N144D.
*Petioles length*.—0.5 cm.
*Diameter of petiole*.—0.2-0.4 cm.
*Texture*.—Slightly pubescent.
*Color of lateral branch*.—RHS 144B, with blotches that are exposed to light of about RHS 187B.
*Length of lateral branch*.—11.0-14.0 cm.
*Diameter of lateral branch*.—0.1 cm.
*Length of internodes*.—0.2-0.5 cm.
*Texture*.—Slightly pubescent.
*Peduncle color*.—RHS 144B, with blotches exposed to more light of about RHS 187B.
*Length of peduncle*.—16.0-18.0 cm.
*Peduncle diameter*.—0.2 cm.
*Texture*.—Slightly pubescent.
*Color of pedicel*.—RHS 144B, with blotches exposed to more light of about RHS 187B.
*Length of pedicel*.—0.5-0.9 cm.
*Diameter of pedicel*.—0.1 cm.
*Texture*.—Slightly pubescent.

Inflorescence:
*Type*.—Simple cyme.
*Quantity of flower stems per rosette*.—2-3.
*Quantity of flowers per flower stem*.—2-6.
*Number of flowers per plant*.—180.
*Lastingness of individual blooms on the plant*.—10 days.
*Lastingness of entire inflorescence*.—10-12 days.
*Natural flowering season in Europe*.—February-May in Europe, depending on climatic conditions.

Bud (when first showing color):
*Color*.—RHS 187B.
*Length*.—0.9 cm.
*Width*.—0.4 cm.
*Shape*.—Orbicular.

Corolla:
*Form*.—Single, solitary, symmetrical; 5 imbricate petals slightly cup-shaped.

Immature:
*Floret horizontal diameter*.—0.4 cm.
*Color upper petals, upper surface*.—RHS 187C.
*Color upper petals, lower surface*.—RHS 187C.

Mature:
*Floret horizontal diameter*.—2.3 cm.
*Floret depth*.—0.5 cm.
*Petal color, upper surface*.—A little lighter than RHS 187D with RHS 187B veins.
*Lower surface*.—RHS 187D with RHS 187C veins.
*Petal length*.—1.0 cm.
*Petal width petals*.—0.7 cm.
*Petal shape*.—Orbicular.
*Apex shape*.—Mostly rounded; acuminate on young flowers.
*Petal base shape*.—Attenuate.
*Margin*.—Entire.
*Petal texture, upper surface*.—Papillose.
*Lower surface*.—Papillose.

Sepals:
*Number of sepals*.—5.
*Color of sepals, upper surface*.—RHS 183A.
*Lower surface*.—RHS N186C.
*Length of sepals*.—0.3-0.4 cm.
*Width of sepals*.—0.2 cm.
*Sepal shape*.—Ovate.
*Apex shape*.—Acute.
*Margins*.—Entire.
*Texture, upper surface*.—Slightly pubescent.
*Lower surface*.—Glabrous.

Reproductive organs:
*Number of stamens*.—10.
*Filament color*.—RHS 185D.
*Filament length*.—0.4 cm.
*Filament diameter*.—Less than 0.1 cm.
*Anther color*.—RHS 149A.
*Anther length*.—0.15 cm.
*Anther shape*.—Oval, bi-lobed.
*Pollen color*.—RHS 154B.
*Pollen amount*.—Normal for the species.
*Pistil*.—2.
*Pistil length*.—0.3 cm.
*Style color*.—RHS 1B.
*Style length*.—0.2 cm.
*Stigma color*.—RHS 183D.
*Ovary color*.—RHS 151A.
*Ovary length*.—0.15 cm.
*Ovary width*.—0.2 cm.
*Fertility/seed set*.—Has not been observed on this hybrid.
*Disease/pest resistance*.—Has not been observed on this hybrid.

What is claimed is:

1. A new and distinct variety of *Saxifraga* plant named 'SAXZ0006' substantially as illustrated and described herein.

* * * * *